(12) United States Patent
Beneda

(10) Patent No.: US 11,534,040 B2
(45) Date of Patent: Dec. 27, 2022

(54) ANTIVIRAL COMMODE

(71) Applicant: Henry Beneda, Lompoc, CA (US)

(72) Inventor: Henry Beneda, Lompoc, CA (US)

(*) Notice: Subject to any disclaimer, the term of this patent is extended or adjusted under 35 U.S.C. 154(b) by 0 days.

(21) Appl. No.: 17/392,952

(22) Filed: Aug. 3, 2021

(65) Prior Publication Data

US 2022/0039621 A1 Feb. 10, 2022

Related U.S. Application Data

(60) Provisional application No. 63/061,642, filed on Aug. 5, 2020.

(51) Int. Cl.
*A47K 13/30* (2006.01)
*F16J 15/32* (2016.01)
(Continued)

(52) U.S. Cl.
CPC ........... *A47K 13/307* (2013.01); *F16J 15/32* (2013.01); *F21V 33/004* (2013.01); *F21Y 2115/10* (2016.08)

(58) Field of Classification Search
CPC ...... A47K 13/00; A47K 13/10; A47K 13/105; A47K 13/24; A47K 13/302; A47K 13/307;
(Continued)

(56) References Cited

U.S. PATENT DOCUMENTS 3,689,944 A * 9/1972 Clayton ................. E03D 9/052
4/213
4,830,791 A * 5/1989 Muderlak ............... E03D 9/052
239/57
(Continued)

FOREIGN PATENT DOCUMENTS

CN 2728395 Y 9/2005
CN 201221125 Y 4/2009
(Continued)

OTHER PUBLICATIONS

"Devilbiss Intellipap CPAP machine Foam Filters". The CPAP Shop. Mar. 9, 2018. <https://www.thecpapshop.com/devilbiss-intellipap-series-reusable-black-foam-filters> (Year: 2018).*
(Continued)

*Primary Examiner* — David P Angwin
*Assistant Examiner* — Nicholas A Ros
(74) *Attorney, Agent, or Firm* — Cynthia S. Lamon; Lamon Patent Services

(57) ABSTRACT

A modular antiviral air filter assembly for filtering displaced air in a toilet has a ventilated filter housing having a bottom sealing surface, a peripheral side wall, and a top lid, the filter housing fixed to or formed contiguously to the underside of the top lid of the toilet, at least one antiviral filter disposed within the filter housing having contact with the displaced air from the bowl of the waste collection utility. The antiviral filter assembly closes and seals against the donut rim seat after use and remains sealed during flush operation of the waste collection utility wherein the displaced air from water filling the collection bowl is filtered through the one or more antiviral filters before egress out of the ventilated portion or portions of the filter housing.

10 Claims, 7 Drawing Sheets

(51) Int. Cl.
*F21V 33/00* (2006.01)
*F21Y 115/10* (2016.01)

(58) Field of Classification Search
CPC ....... E03D 5/04; E03D 5/10; E03D 9/04–052; E03D 5/105
See application file for complete search history.

(56) References Cited

U.S. PATENT DOCUMENTS

| | | | | |
|---|---|---|---|---|
| 5,170,516 A | * | 12/1992 | Davison | A47K 11/00 297/188.09 |
| 5,539,937 A | * | 7/1996 | Barefoot | A47K 13/307 4/213 |
| 6,895,604 B1 | * | 5/2005 | Ramsey | A47K 13/307 4/213 |
| 7,730,559 B2 | * | 6/2010 | Gallizia | E03D 9/05 4/213 |
| 7,976,600 B1 | * | 7/2011 | Safuto | A47K 13/24 4/371 |
| 10,201,198 B2 | * | 2/2019 | Tong | C09D 5/14 |
| 2010/0313890 A1 | * | 12/2010 | Messier | B01D 39/1623 128/206.19 |
| 2012/0090082 A1 | * | 4/2012 | Nwankwo | A47K 13/105 4/246.1 |
| 2012/0144569 A1 | * | 6/2012 | Kodat | E03D 9/005 4/222 |
| 2013/0031799 A1 | * | 2/2013 | Gagnon | A47K 10/48 34/79 |

FOREIGN PATENT DOCUMENTS

| | | | | |
|---|---|---|---|---|
| CN | 106821127 A | | 6/2017 | |
| CN | 107049122 A | | 8/2017 | |
| CN | 107806140 | * | 3/2018 | ............... E03D 5/10 |
| CN | 108078476 A | | 5/2018 | |
| GB | 2552311 | * | 1/2018 | ............. A47K 13/24 |
| WO | WO02100235 | * | 12/2002 | ............. A47K 13/00 |
| WO | WO2004100745 | * | 11/2004 | ............. A47K 13/00 |

OTHER PUBLICATIONS

"SleepMD BIPAP". SleepMD. Sep. 29, 2020. <https://www.sleepmd.net/bidirectional-positive-pressure-bipap/> (Year: 2020).*

"Devilbliss Intellipap CPAP machine Foam Filters". The CPAP Shop. Mar. 9, 2018. <https:/Avww.thecpapshop.com/devilbiss-intellipap-series-reusable-black-foam-filters> (Year: 2018).*

"SleepMDBIPAP".SIeepMD.Sep. 29,2020.<https:/Avww.sleepmd.net/bidirectional-positive-pressure-bipap/> (Year: 2020).*

* cited by examiner

ANTIVIRAL COMMODE

CROSS-REFERENCE TO RELATED DOCUMENTS

The present invention claims priority to a U.S. provisional patent application No. 63/061,642 entitled "Anti-Aerosol Toilet Seat" filed on Aug. 5, 2020, disclosure of which is included in this specification at least by reference.

BACKGROUND OF THE INVENTION

1. Field of the Invention

The present invention is in the field of plumbed waste collection facilities and pertains particularly to methods and apparatus for removing contaminants from displaced air in a plumbed waste collection facility.

2. Discussion of the State of the Art

In the art of waste management, there are a plethora of utilities and equipment designed or otherwise adapted to collect human biological waste safely and/or treat and recycle the human biological waste, hopefully, eliminating or at least reducing potentially harmful biological airborne contaminants and/or potentially harmful airborne synthetic toxins and/or fumes.

A typical system for recycling biological human waste like feces and urine includes a collection process, for example, collecting waste via toilet and urinal. Human waste may be stored in collection tanks known as septic tanks for periodic collection by vehicle. Human waste may be collected and pumped into a sewer system eventually arriving at one or more treatment facilities where chemicals and certain processes may be applied to the wastewater to clean it from biological and synthetic contaminants. The treated water may then be used in other applications or may be released into the natural water drainage system.

It is known in the art and confirmed by many studies performed that a waste collection utility like a flush toilet, for example, may allow for airborne particles specific to disease causing spores, viruses, and other airborne contaminant materials be distributed into the air surrounding the flush toilet. Such contaminants may remain airborne for a period before they settle on surfaces around the flush toilet including the toilet surfaces, counter tops, sinks, shower units or bath unit surfaces, etc.

In a study referred to herein as Wilcox, Sandoe, and Best, entitled "Potential for Aerosolization of *Clostridium difficile* after flushing toilets" found that *C. difficile* was recoverable from air samples after a flushing operation on a toilet. The samples taken were positive for *C. difficile* at 25 centimeters above the toilet seat. Bioaerosols produced by toilet flushing potentially contribute to hospital environmental contamination. Prevention measures (toilet lids) should be evaluated as interventions to prevent toilet-associated environmental contamination in clinical settings.

Other studies reveal that Toilets must be kept clean to prevent the transmission of bacteria and pathogens during the outbreak of the novel corona virus epidemic. Toilet users' health can be affected by pathogens embedded in airborne aerosol droplets that may rise as high as one meter from the toilet seat during flushing and spread in the air. Each toilet flush can produce approximately 14,000 to 80,000 aerosol droplets, which can rise higher if the water tank is installed on a high position or a valve type flushing system is used.

The droplets may rise as high as one meter. Their study revealed that pathogens can be spread in the air by aerosol droplets emitted from toilet flushing, thus contaminating the washroom. Also, the smaller the size of the pathogens, the higher the concentration of distribution in the air after flushing. Covering the toilet lid before flushing can help to reduce bacteria-embedded airborne aerosol droplets that may contaminate the air and the washroom; however, Professor Lai said international studies found that bacteria can still be emitted from toilet flushing as there is a space of a few millimeters between the lid and the toilet bowl.

Multiple flushing may not help eliminate this problem since pathogens can stay on the surface of the toilet bowl for some time and be transmitted with aerosol droplets. The room walls and all surfaces and surrounding area will thus be infected when pathogens are spread in the air from a flushing event. As a result, the toilet lid, wash basin and even the floor of the washroom will be contaminated. Typically, a recommended bleach or sanitizer solution is to use 1 to 49 diluted household bleach to regularly clean the toilet bowl and 1 in 99 diluted household bleach to clean all areas of the washroom. Use the exhaust fan, if available, for 15 to 30 minutes after using the washroom to help dilute the bacteria and virus in the air. An opened window will also maintain adequate indoor ventilation.

In practice, a flushing of a typical toilet utility causes displacement of air within the toilet bowl by the additional water entering the toilet bowl, the added water being flushed out of the bowl causes air to come back into the bowl, and the added water after flushing causes the air in the bowl to be displaced out again. Typically, the aerosolized plume of biological material is pushed upward, however, it may also be pushed laterally if a toilet lid is closed due to a gap around the toilet lid underside and the toilet bowl rim. Scientific discovery that sewers may contain viruses such as the SARS Covid-19 virus as well as other pathogens confirms that those pathogens are present when the infected person uses the toilet facility and, therefore, may be aerosolized into the immediate area of the toilet and after time may settle on virtually all of the surfaces in the immediate area of the toilet.

An obvious problem with the devices known in the art is that they rely on known in the art sensors analyzers, collectors, filters, or sanitizers. Prior art devices are non-electric, a non-mechanical, and non-moving devices. They are also not airtight preventing all aerosols. Further to the above challenges, aerosolized or airborne contaminants, spores, or pathogens may bypass around the edges of the depicted article which may only be retained within a housing and not scaled off from hollow space above and peripheral to the toilet.

Therefore, what is clearly needed in the art is a modular antiviral filter assembly for filtering airborne containments from air displaced during a flushing sequence of a waste collection facility that removes, contains, or eliminates inorganic and organic airborne particles including viral pathogens emanating.

BRIEF SUMMARY OF THE INVENTION

According to an embodiment of the invention, a modular antiviral air filter assembly for filtering displaced air in a toilet is provided and includes a ventilated filter housing having a bottom sealing surface, a peripheral side wall, and a top lid, the filter housing fixed to or formed contiguously to the underside of the top lid of the toilet, at least one antiviral filter assembly disposed within the filter housing having contact with the displaced air, the at least one antiviral filter assembly including at least one antiviral filtering medium, a gasket attached to or otherwise formed on the underside of a donut rim seat of the toilet, the gasket contacting the rim surface of the collection bowl or basin of the toilet, and a user operated handle attached to or formed on the surface of the top lid characterized in that the antiviral filter assembly closes and seals against the donut rim seat after use and remains sealed during a flush operation of the toilet wherein the displaced air from water filling the collection bowl is filtered through the one or more antiviral filters before egress out of the ventilated portion or portions of the filter housing.

In one embodiment, the toilet is a public or a private commode. In one embodiment, the one or more antiviral filter are continuous positive airway pressure (CPAP) filters. In one embodiment, the one or more antiviral filters are bi-directional positive airway pressure (BIPAP) filters. In one embodiment, the antiviral filter is an annular air filter customized for trapping bacteria and viruses. In one embodiment, the air filter assembly has a wireless electronic control module (WECM) disposed within a compartment inside the filter housing, the control module communicating with an automatic electric flushing unit adapted to initiate flushing when a signal or sensor informs or detects that the top lid of the assembly is in a closed position after use of the waste collection utility. In one embodiment, the air filter assembly includes two or more light emitting diodes (LEDs) for alerting a user to whether or not it may be safe to open the top cover again after a flush. In a preferred embodiment, the donut seat has a bottom peripheral inside skirt with an angled sealing surface that mates flush with a complimentary angled sealing surface disposed about the bottom peripheral edge of the filter housing with the top lid closed, the seal method surface-to-surface or groove and O-ring gasket.

In one embodiment, the ventilated filter housing includes vents in the form of one or more arrays of parallel through slots arranged strategically and disposed proximal to the rear portion of the side wall of the filter housing. In one embodiment, the donut seat is relieved of some material at top center of the seat to enable the top cover to be lifted off the donut seat without a handle. In an embodiment using a WECM and an electric flushing unit, the automated flushing function initiated by the electric flushing unit is initiated with the top lid open after a period if the top lid is not closed after use. In one embodiment, the air filter assembly includes at least one electrostatic precipitator disposed inline at top and or beneath the filter material in the one or more airflow filters. In a variation of this embodiment, the electrostatic precipitator(s) include zinc and copper rings deposited concentrically on a substrate or copper and silver dots deposited in a matrix on a substrate. In variations of this embodiment, the substrate is a cloth material, a polymer material, or a material blend thereof. In one embodiment using a WECM and an electric flushing unit, the air filter assembly includes a charging port for charging the WECM.

DETAILED DESCRIPTION OF THE INVENTION

In various embodiments described in enabling detail herein, the inventor provides a unique system for eliminating viral or pathogenic plumes from emanating from commodes during flushing. A goal of the present invention is to reduce or eliminate or contain viral or other pathogenic microbes, spores, and other contaminants from air forced out of a commode bowl during the flushing operation. Another goal of the invention is to prevent unnecessary spread of airborne viruses and other airborne contaminants to a group of people that use restroom facilities. The present invention is described using the following examples, which may describe more than one relevant embodiment falling within the scope of the invention.

Figure 1B:
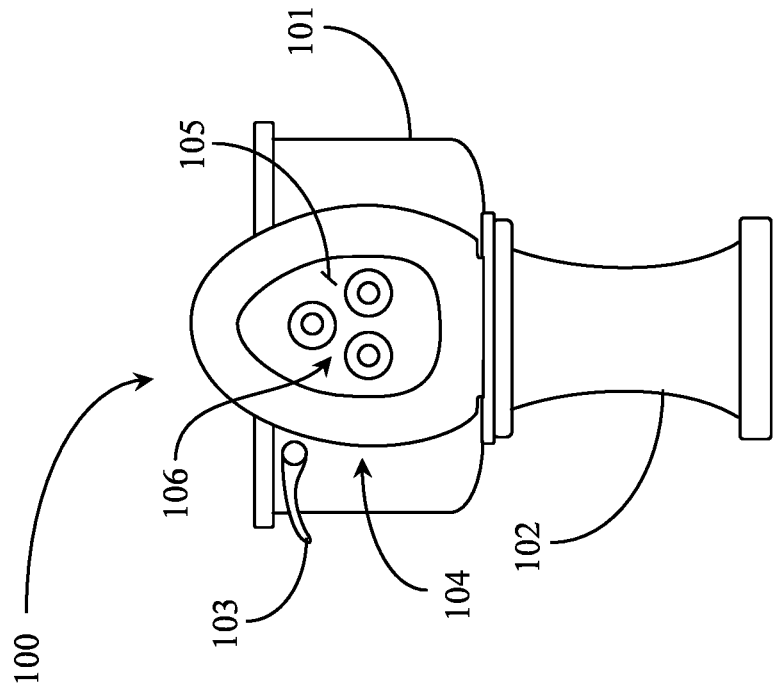
FIG. 1B is a front elevation view of the antiviral commode of FIG. 1A with lid open.
Figure 1A:
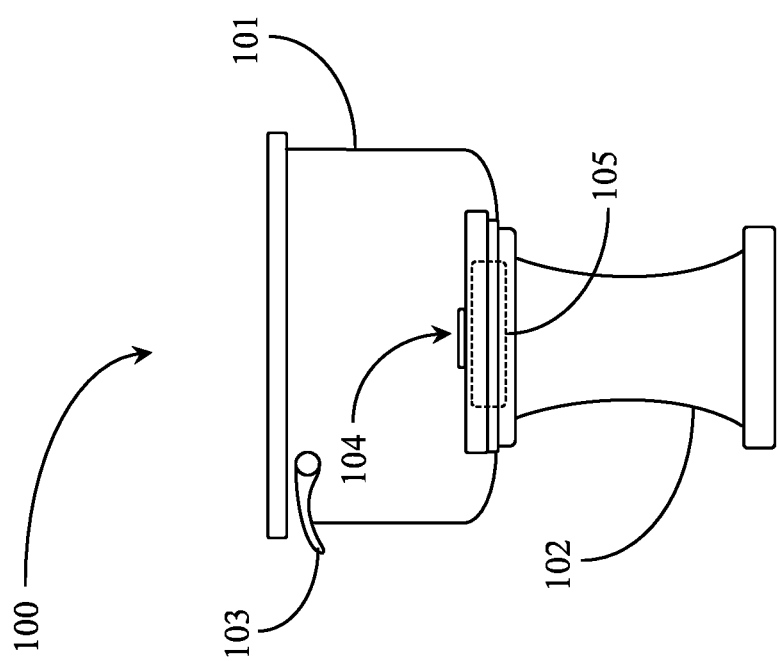
FIG. 1A is a front elevation view of an antiviral commode with lid down according to an embodiment of the present invention.

FIG. 1A is a front elevation view of an antiviral commode facility 100 with lid down according to an embodiment of the present invention. Antiviral commode 100 is a home use version of the present invention. Commode 100 includes a base structure 102 including the collection basin or bowl having a commode rim as all commode systems have. Commode 100 includes a water tank 101 set behind commode 100 for holding water for flushing purposes. Commode 100 is manually flushed in this embodiment using a flush handle 103 connected to a typical internal chain, float, and stopper assembly typical of household commode systems. As referenced in the background section of this specification, a problem exists when a person who may be shedding airborne pathogens such as a transmissible airborne virus, for example, uses the facility and flushes commode 100 whether the commode lid is up or down when flushing occurs. The problem is that the flushing process dumps water from tank 101 into the bowl inside base structure 102 thus displacing air upward and outward in a plume. Any airborne pathogen may be carried for some time in the ejected plume and may eventually settle after a period onto a surface near the facility. In this case, some pathogenic materials may still retain a capability of infecting another person that comes in contact with such bathroom surfaces after the person has used the facility.

According to one embodiment of the invention, the inventor provides an antiviral lid assembly 104 that may be operated to reduce or eliminate pathogens that may wind up in the humid air plume forced out of the commode bowl during the flushing process. Assembly 104 encompasses a donut commode seat and lid that are modified or otherwise manufactured to support an antiviral filter housing 105 that may be installed on the underside of the top lid and that may seal against the inside rim of a modified donut seat that rests on the bowl rim of base structure 102. Although not visible in this embodiment, the donut seat may also be modified by an addition of gasket material on the underside surface thereof for sealing against the top rim of the collection bowl inside base structure 102. In one embodiment of the present invention, assembly 104 may be manufactured and sold to consumers as an aftermarket antiviral solution for reducing or eliminating airborne pathogens that may otherwise escape the bowl feature whether the commode lid is in the up position or in the down position while flushing occurs. In such a case, the consumer may replace the existing seat assembly with the antiviral seat assembly 104. In this case, no modifications are required to other components of commode facility 100. In one embodiment, the top lid of antiviral seat assembly 104 includes a lift handle for user convenience in lifting and lowering the top lid supporting filter housing 105. In another embodiment, filter housing 105 may be installed to an existing seat assembly with specific modifications required to successfully integrate the filter housing into the commode seat assembly. In a preferred embodiment, antiviral seat assembly 104 is manufactured and added to an existing commode facility replacing the old seat assembly for user convenience; however, that is not specifically required to enable the present invention.

FIG. 1B is a front elevation view of antiviral commode 100 of FIG. 1A with lid open. In this view of commode facility 100, the top lid of antiviral seat assembly is raised depicting the underside of antiviral filter housing 105. Filter housing 105 may be molded from a polymer material or polymer-rubber composite material that has some density and weight such as an acetal homopolymer material like Delrin™ or a similar composite. Filter housing 105 includes one or more, in this case three, antiviral air filters 106. Antiviral air filters 106 may be continuous positive airway pressure (CPAP) type antifungal/antiviral/anti-particulate filter that may be modified in this embodiment for use as a filter array in filter housing 105. It is noted herein that the underside of filter housing 105 is not amenable to air flowing upward and therethrough the exception of course is directed to air flowing into and through the CPAP filters 106. It may also be noted herein that at least a portion of filter housing 105 is hollowed out on the inside above filters 106 to enable filtered air to flow out from the filter housing through side vents located at the rear portion of the housing that are not visible in this embodiment but may be assumed present. Modified CPAP filters may be considered bi-directional filters meaning that air my flow both directions through the filter device. This is duly noted as the flushing process initiated by handle 103 may force air upward and out of the bowl as the bowl fills with water and may draw air back into the bowl as the water is drained out through the bottom of the bowl during the flushing process. More detail about modifications to CPAP filters 106 is provided later in this specification. Referring back to FIG. 1A, filter housing 105 may extend below the donut seat for some distance from the geometric plane where the filter housing component seals against the inside rim of the donut seat without departing from the sprit and scope of the present invention. In one embodiment, a handle may be provided on the top lid at center front to assist a user in lifting the lid and mounted filter housing off of the donut seat.

Figure 2:
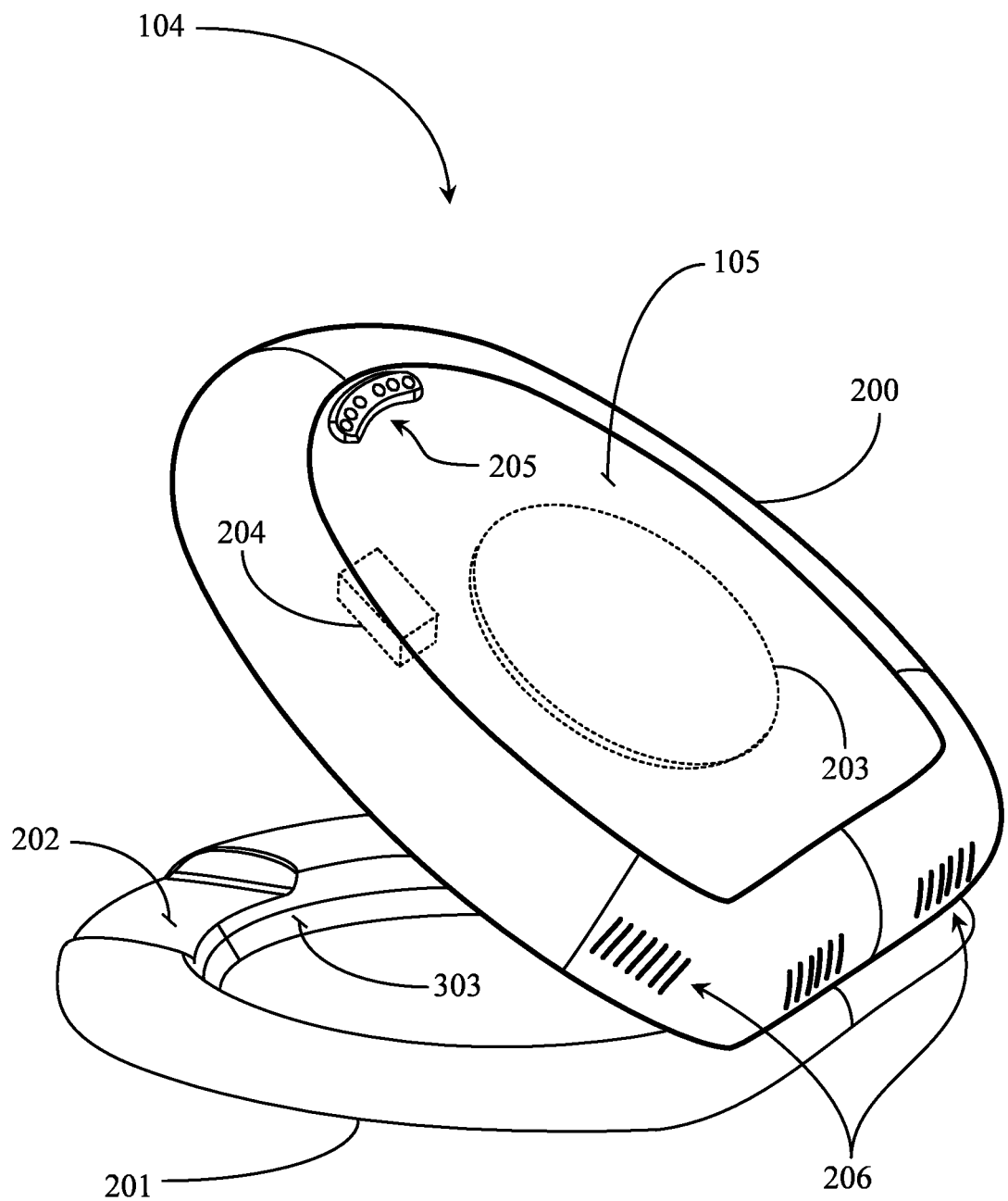
FIG. 2 is an overhead perspective view of a seat assembly of an antiviral commode according to an embodiment of the present invention.

FIG. 2 is an overhead perspective view of seat assembly 104 of antiviral commode 100 according to another embodiment of the present invention. In this embodiment, antiviral seat assembly 104 includes one or more modifications that may be different than the antiviral seat assembly of FIG. 1A and FIG. 1B; however, the same element numbers are given for the assembly and filter housing as the overall primary function of the assembly is the same. In this embodiment, filter housing 105 is mounted to a seat assembly top lid 200. Top lid 200 may have a molded form that overlaps filter housing 105 and that overlaps a donut seat 201 which is modified or otherwise formed to seal against the rim top surface of the commode bowl and on the inside rim in the form of a perimeter skirt 303 formed on the interior opening of the donut seat 201. Skirt 303 may be formed inward (toward center) at an angle of approximately 45 degrees from the plane of the seat that conforms to a seal surface (not visible) created on the outside lower perimeter of filter housing 105 that is complimentary in angularity at 135 degrees and mates flush to skirt 303 when top lid 200 is lowered all the way down. In one embodiment, the seal is a surface-to-surface seal that is sufficient to eliminate any potential gap between the housing filter and the donut seat. In one embodiment, an O-ring gasket may be provided between the filter housing 105 and the donut seat 201. It is noted that the handle mentioned further above may aid a user in pulling up lid 200 from donut seat 201. In this embodiment, donut seat 201 is modified or otherwise formed to include a geometric depression feature 202 on the top at roughly front and center of donut seat 201. Depression feature 202 may function as a symmetrical crevasse feature between seat 201 and top lid 200 enabling a user to lift up on top lid 200 without the use of a handle installed on the top lid.

In this embodiment, antiviral filter housing 105 may host a single larger diameter antimicrobial, antiviral filter 203 (logically represented by broken boundary). In this embodiment, antiviral assembly 104 may be added to a public commode that is flushed automatically using wireless sensor technology. In one embodiment, antiviral seat assembly 104, more particularly, antiviral filter housing 105 may include a wireless electronic control module (WECM) 204 adapted for close range wireless communications with an automated all electric flushing unit that generates an automated flushing command based on sensor data describing a state or condition relative to the commode and the operation thereof by a user. Top lid 200 includes an array 205 of light emitting diodes adapted to inform a user about state of the antiviral commode. In one example, flushing is not performed until the top lid 200 and antiviral filter housing 105 are closed and sealed to donut seat 201. In such a case, one or more states for the antiviral commode may be worked into a routine for flushing that is optimized for the antiviral commode. In a simple form, a red LED or LEDs may turn on and or flash indicating a flushing process has begun, preferably just after a user as closed lid 200 supporting antiviral filter housing 105 over donut seat 201. This action of closing the lid may be communicated to the electric flushing unit (not illustrated) charged with flushing that individual commode in a number of ways without departing from the spirit and scope of the present invention.

In one embodiment, when the person steps away and closes the top lid before flush, the electric flushing unit sees that using an optical sensor and initiates flush when the antiviral filter housing is in correct interface with the donut seat. In another embodiment, when top lid 200 is up, it is communicated to the electric flushing unit by a trip sensor installed proximal to the hinge connection of the top lid and donut seat. An optical laser may be provided as a trip sensor whereupon the line may be broken when the lid is up and unbroken when the lid is placed down. More detail about process relative to flushing is provided later in this specification. In one embodiment wherein antiviral seat assembly includes WECM 204 and or LED array 205, a small power source (not illustrated), which may or may not be a rechargeable power source, may be provided to power electronic functions of the antiviral seat assembly 104. Small batteries might be housed within antiviral filter housing 105. For a rechargeable battery, a charge port may also be provided for charging the power source. In one embodiment, one or a pair of LEDs in LED array 205 may illuminate red for low battery and green for fully charged.

In one embodiment, one or a pair of LEDs in LED array 205 may illuminate red for flush in process (do not open) and green when it is safe to open the top lid 200 after a flush. A counter may be used by the electric flushing unit to correctly define the start and end of every use session of the commode keeping track of use, particularly the raising and lowering of top lid 200. In one embodiment, the electric flushing unit may have a timer function that allows for actions to be deemed authentic, for example, so a user could not open and close top lid 200 quickly expecting to initiate a flushing process each time the top lid 200 was closed. Similarly, the electric flushing unit in the public version of the commode seat assembly 104 may include fall back routines, for example, if a user simply walks away and does not close top lid 200, the unit may initiate a flush after a set period wherein the top lid 200 is detected not to be closed, and no person is detected in the stall, or immediate area around the public version.

Top lid 200 includes multiple air vents 206 (three vents visible) disposed to the rear end and rear sides of the unit. Air vents 206 each may include a number of parallel through slots that are placed through the body of top lid 200 and through the body of filter housing 104 at the upper hollow portion of the housing above the top plane of the filter 203 or filter array 106 of FIG. 1B (home version). It may be noted herein that either filter design described above may be used in a public version of the commode or in a consumer home version of the commode without departing from the spirit and scope of the invention. In a preferred use embodiment, air forced out of the commode bowl during a flush is forced through antimicrobial air filter 203 into a hollow spaced above the filter, the filtered air allowed to exit through air vents 206. Antimicrobial filter 203 may be a bidirectional filter allowing air that exited through vets 206 to be drawn back through filter 203 and exiting into the commode bowl when the water that filled the bowl is drained from the bowl during the flushing operation. Filter 203 may be removed and replaced as necessary: about every 6 months of operation.

Figure 3:
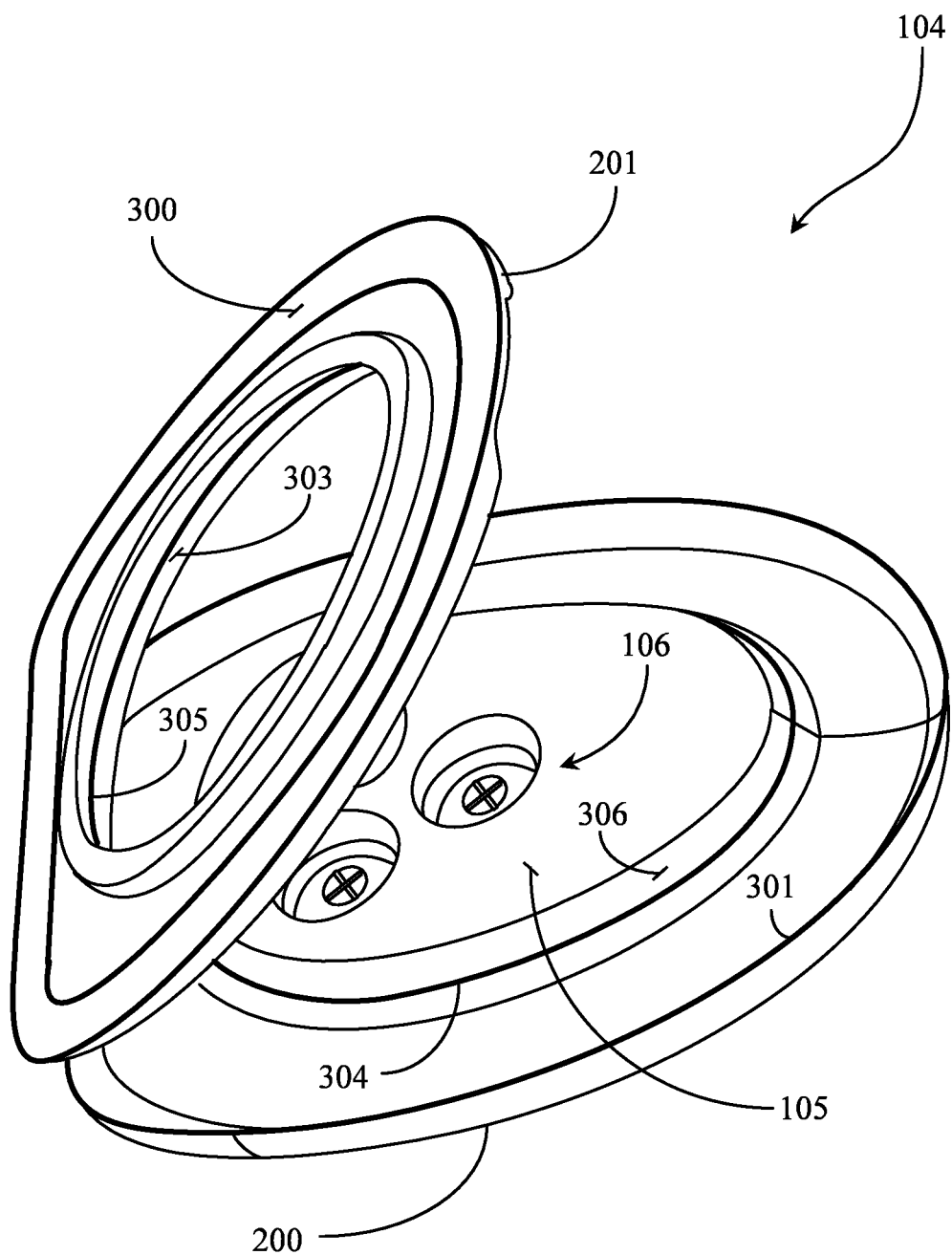
FIG. 3 is an underside perspective view of a seat assembly of an antiviral commode according to an embodiment of the present invention.

FIG. 3 is an underside perspective view of seat assembly 104 of antiviral commode 100 according to the embodiment of FIG. 1. In this embodiment, the filter design includes three CPAP filters in array 106. The filters in array 106 may be bi-directional positive airflow (BIPAP) filters meaning air may flow through them in both directions conforming to the bi-directional air displacement occurring in the commode bowl during the flushing process. Top lid 200 may be molded or otherwise formed having a peripheral downward facing wall 301 that may overhang the perimeter of donut seat 201 by some distance. Filter housing 105 may have a perimeter surface 306 that is formed at an angle complimentary to skirt surface 303 such that when brought together the surfaces mate and are flush to one another to a tolerance of about one degree or less across the mating surfaces providing a sealing interface that eliminates an air gap typically located between a top lid and donut seat in prior art seat assemblies not modified to practice the invention. In one embodiment, sealing surface may include a peripheral groove feature 305 that may accept an O-ring gasket 304. Groove 305 may extend peripherally about the angled surface of skirt 306.

The technology of surface-to-surface sealing is well known in the art and the desired seal affect may be had whether an O-ring gasket is provided or not; however, sealing by gasket may allow for a less strict angular tolerance in manufacturing the angled surface interface between the inner skirt 303 and the angled surface 306 around the lower portion of filter housing 105. In one embodiment, a commode kit containing the antiviral seat assembly may include two gaskets 300 and 306. In this embodiment, donut seat 201 has a flat and wide gasket 300 adhered to the underside of the donut seat and adapted to provide a seal against the top surface of a commode bowl rim. Gasket 300 may be glued to the underside of donut seat 201. Gasket 300 may be a silicon rubber gasket material that is somewhat pliable but resilient and that has a thickness sufficient to provide a sealing surface against the commode rim under the added weight of top lid 200 created by the addition of the filter housing. Gasket 300 eliminates a typical gap between the donut seat and the top rim of the commode bowl found in unmodified commodes with seat assemblies, which are not adapted to practice the invention. Gasket 306 provides a similar seal between the top lid 200 and the seat 201.

The purpose of using gaskets and or sealing surfaces is to ensure that contaminated air from the commode bowl does not escape into the atmosphere around the commode through any gaps in the system and must instead travel through the filters provided in filter housing 105. It is noted herein that top lid 200 should be closed over donut seat 201 against the rim of the commode bowl as soon as possible after waste is collected. The bidirectional nature of the filters and the flushing process may allow also for air that might have escaped before the lid was closed to be drawn back into the system during the flushing process at least greatly reducing the number of contaminants in the air around the commode that would eventually settle onto bathroom surfaces about the commode.

Figure 4:
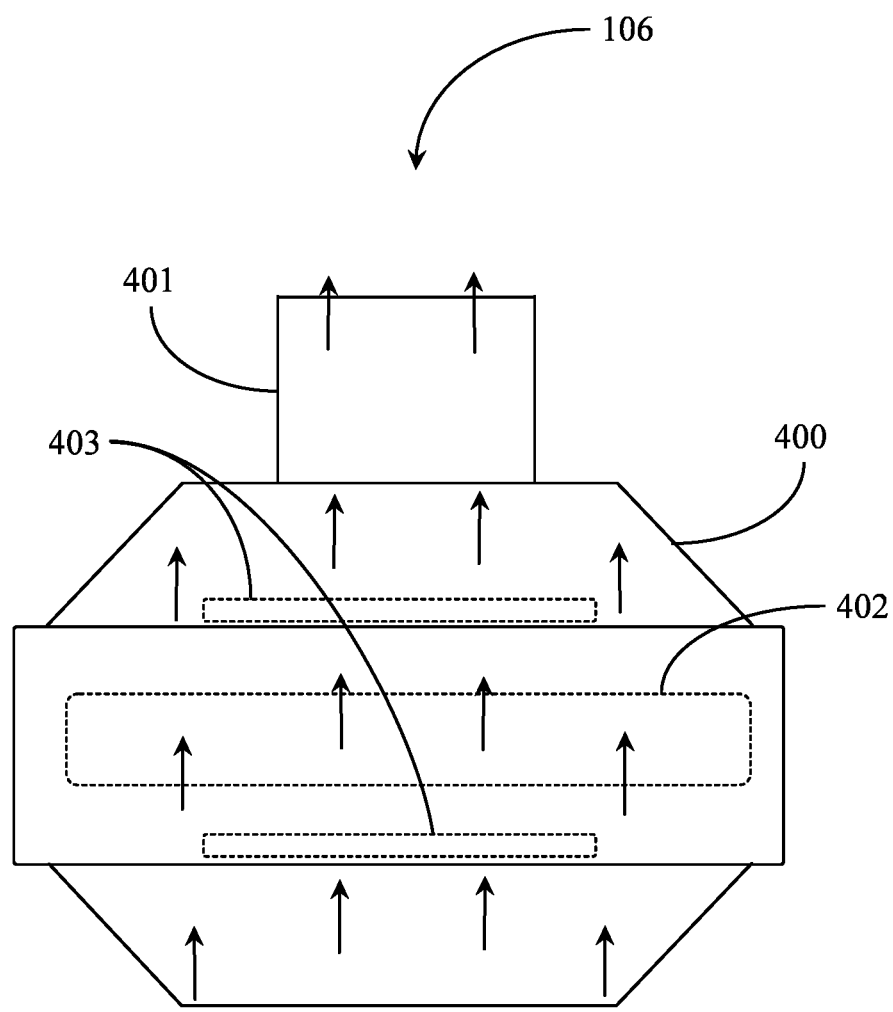
FIG. 4 is a front elevation view of a CPAC filter modified for a seat assembly of an antiviral commode according to an embodiment of the present invention.

FIG. 4 is a front elevation view of a CPAP filter modified for seat assembly 104 of antiviral commode 100 according to an embodiment of the present invention. Filter assembly 106 may be a CPAP or BIPAP filter that is modified to practice the present invention. Filter assembly 106 is adapted as a removable and replaceable filter inserted into and annular cavity provided through the bottom solid portion of filter housing 105. An array of such filters may be provided wherein each filter has its own airflow channel. In the embodiment of FIG. 1B there are three filters in the array; however, there may be more or fewer filters incorporated into the filter housing without departing from the spirit and scope of the present invention. Filter 106 includes an annular polymer or plastic casing 400 having a disk-like central annular portion that houses a microbial/viral filter 402 (CPAP/BIPAP)) and adjacent prefilters 403 one above filter material 402 and one below filter material 402.

Prefilters 403 may, in one embodiment, be fabricated of cloth or plastic substrate with alternating concentric metallic rings of zinc and copper separated by a thin uniform gap.

Zinc and copper may be printed or otherwise deposited on the annular substrate, which may be referred to as a nanoplate. Prefilters 403 may be termed electrostatic precipitators in the art. Electrostatic precipitators may also include electric disinfectant capabilities and are annular inserts into the otherwise unmodified CPAP or BIPAP filter assembly 106. Prefilters 403 are adapted to remove bacteria during the in-and-out airflow of the commode flushing process. The gap between the concentric zinc and copper rings referred to as nanoplates creates an electric current whenever ionic moisture is aerosolized during the commode flush operation, the current electrocuting bacteria, virus, microbes, etc. within the created circuit.

Precipitators create a weak electrical field in the presence of humidity in the air traveling through the CPAP or BIPAP filter device as mentioned above. In addition to the filtering action of the central microbial filter material 402, prefilters 403 may eliminate airborne viruses on contact through a weak electrocution process. Zinc is a well known antibacterial and antifungal compound that in the form of zinc pyrithione may be incorporated into cloth material, in this case in the form of a ring. Cooper salt may be used to form the copper rings on the cloth material. Copper is often used in disinfectants and has antimicrobial properties. In one embodiment, the substrata for the zinc and copper rings may be plastic instead of cloth without departing from the spirit and scope of the invention. In another embodiment of the present invention, prefilters 403 may include metallic spots of zinc and silver, silver replacing copper, in a dot matrix printed or otherwise deposited on cloth, fabric, plastic, or synthetic blend of materials wherein the silver dots bound each copper dot in the matrix on four corners. Essentially, the dot matrix works in the same fashion as the concentric rings in the presence of ionized moisture or humidity in the aerosolized water traveling through the filter housing 105 (from FIG. 1A). In one embodiment the prefilters 403 may be viral cidal nano copper disks that are insertable in into the filter casings.

Filter assembly 106 has its own airflow channel architected through casing 400 and is open at both ends to facilitate airflow including an annular section 401 (short pipe) at the top of the filter assembly. Section 401 empties out inside the hollowed portion of the filter housing 105 and is directed toward the rear of the housing where vents 206 introduced further above in FIG. 2 are located. On a flush operation water fills the void in the commode bowl causing a plume of air to rise up vertically through filter assembly 106 in the direction of the arrows. As the air is passing through the channel it contacts prefilters 403 and antimicrobial/antiviral filter material 402. It is duly noted herein that after the plume rises due to pressure from water filling the bowl just before draining, the sudden removal of the extra water from the bowl causes the airflow to reverse in direction causing filtered air and ambient air to flow back through the filter element 402 and to contact prefilters 403 again. Lastly, the commode bowl may, just after draining, be refilled again to a planned depth causing the airflow to reverse again back upward giving ample contact of airborne contaminants to the prefilters 403 and through filter material 402 at rough center of the vertical channel extending through the filter assembly 106. In one embodiment, filter housing assembly 105 may include a small air fan that may be powered on during the flushing process that may help to move rising air through the filter channels or channel in the case of a single filter. Such a fan may be programmed to also reverse air flow back into the commode bowl at the correct time when water is drained from the bowl. LEDs 205 (FIG. 5) in the top lid 200 may illuminate red at the beginning of the flushing process and then green at an appropriate time after flushing (5 to 7 seconds) whereby the user may open lid 200 breaking seal with the skirt 303 (FIG. 3) formed about the bottom of the opening in donut seat 201 (FIG. 3).

Figure 5:
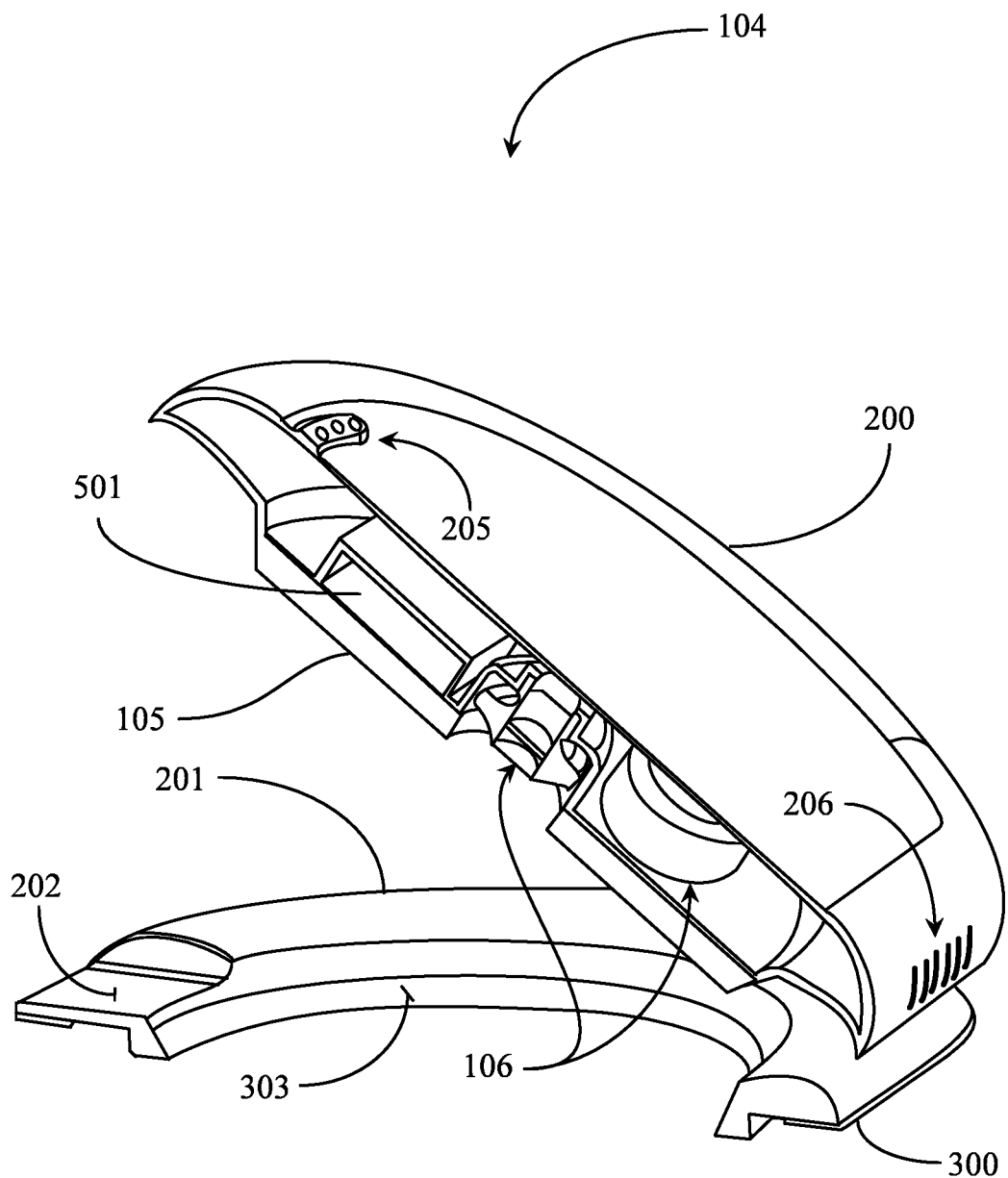
FIG. 5 is a sectioned perspective view of an antiviral commode seat assembly according to an embodiment of the invention.

FIG. 5 is a sectioned perspective view of antiviral commode seat assembly 104 of FIG. 3 according to an embodiment of the invention. In this sectioned view, the hollowed portions of filter housing 105 are depicted. In one embodiment, filter housing 105 and top lid 200 are molded as one contiguous article. In another embodiment, filter housing 105 is a separate article that is mounted to the underside of top lid 200 in a fashion that creates the hollow portions of the assembly. The bottom portion of filter housing 104 is thicker material that supports weight and a complimentary surface 306 (FIG. 3) not visible, that mates flush with angle skirt surface 303 on donut seat 201. Filters 106 are depicted with one filter casing dissected in this section showing internal architecture for staging the filter elements. A single air vent 206 is visible in this view. A compartment 501 is provided in this embodiment to house a wireless control module like WECM 204 of FIG. 2 above. In one embodiment, other electronics such as a battery source to power LEDs 205 and or the WECM is provided within the filter housing. In one embodiment WECM has an onboard power source in the form of a rechargeable battery. In a further embodiment, a charge port such as a mini universal serial bus (USB) port may be provided for the purpose of remotely charging the unit from an external battery or power source. In this embodiment, the hollowed portion of antiviral filter housing 105 extends the full length of the housing down to the interfacing floor of the housing wherein annular CPAP filters are contained in solid pillars open at both ends that stop short of the full height of the inside of the filter housing to enable the air to pass completely through into the hollow portion of the filter housing.

In this embodiment, gasket 300 seals against the upper rim surface of a commode bowl and the skirt extends below the rim surface of the commode bowl. Depression feature 202 may provide a convenient location to lift top lid 200 breaking the seal between the filter housing 105 and the donut seat 201. In a preferred embodiment, no air may pass into filter housing 105 from the commode bowl without traveling through the provided filter or filters. It may be assumed that the treated air may exit filter housing 105 through vents in the filter housing like vent 206. In this embodiment, the WECM may include an onboard battery that may also power the LED panel 205. It may be reminded that top lid 200 integrated with filter housing 105 is hinged to donut seat 201 at the rear (hinge not illustrated). In one embodiment, donut seat 201 is made of solid material like plastic and may be molded or otherwise formed.

Figures 6A, 6B:
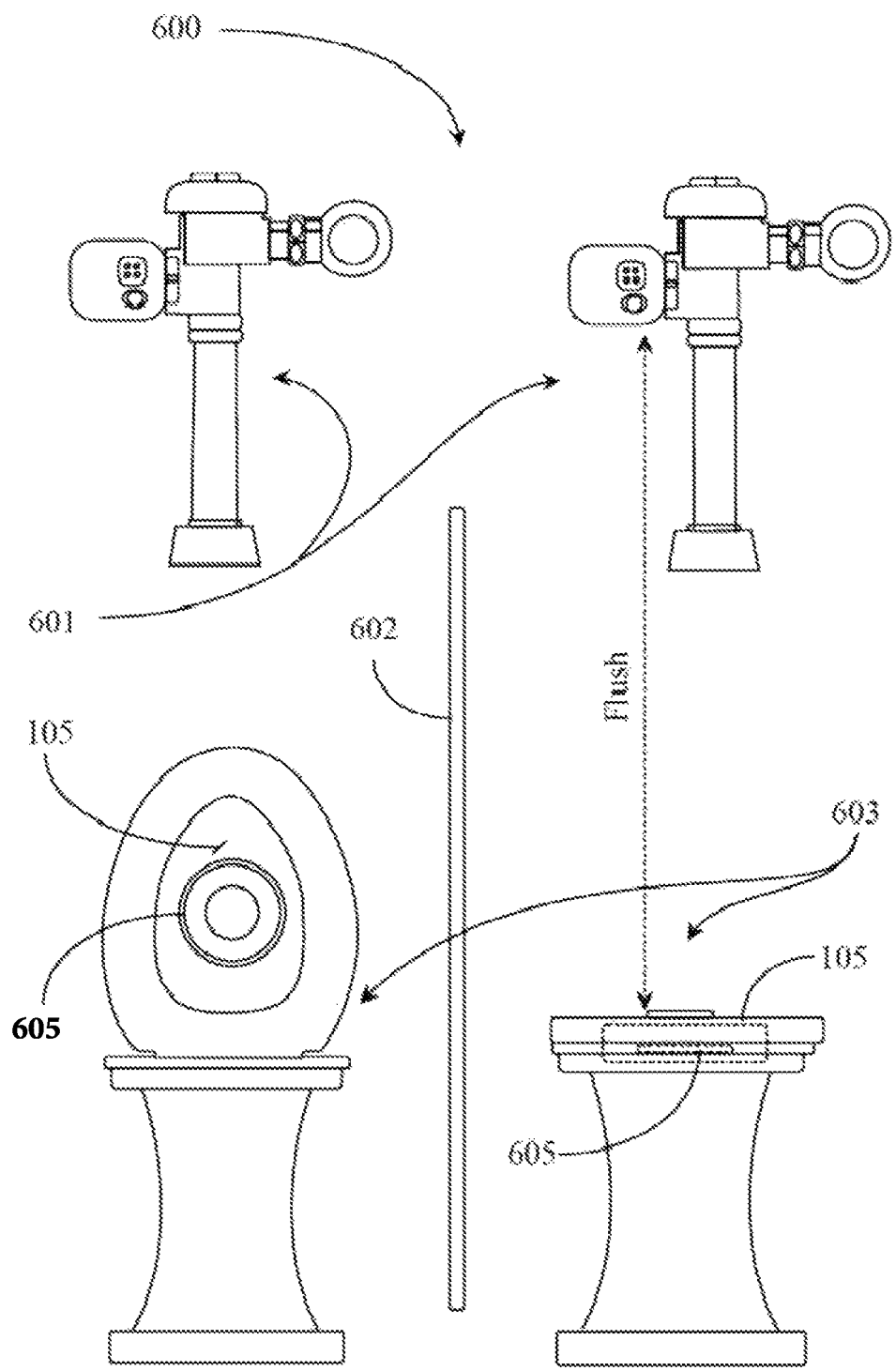
FIG. 6A is a block diagram depicting one of two antiviral commodes used in a public facility according to an embodiment of the invention.
FIG. 6B is a second one of the antiviral commodes used in a public facility according to an embodiment of the invention.

FIG. 6 is a block diagram depicting a public facility 600 of antiviral commodes according to an embodiment of the invention. Public facility 600 may include one, two, or more commodes 603 depending upon the type of public restroom facility it is. A rest stop facility may have several commodes 603 whereas a gas station facility or park and recreation facility may have fewer commodes 603. In this embodiment, public commodes are separated from one another at least by a partition 602 for purposes of privacy. Each commode 603 includes an antiviral seat assembly 104 analogous to the assembly 104 of FIG. 2 wherein a single microbial/antiviral/antifungal filter 605 is provided in place of modified CPAP/BIPAP filters. Filter 605 is analogous to filter 203 introduced in FIG. 2 above and is supported in an annular airflow channel that may be several inches in diameter. Similarly, the total airflow channel footprint of three separate CPAP/BIPAP filters may be similar or several inches in aggregate. Each public commode 603 may be paired wirelessly with dedicated all-electric flushing units 601. Tankless commodes are flushed directly through water supply lines (pipes not visible) as opposed to gravity-based tank systems that store a gallon or so of water to drop into the commode bowl. Flushing units 601 may be adapted with smart sensor technology, for example, that flushes the commode when the user steps out of optical recognition of the sensor, however, to practice the invention, the flushing must be initiated when the seat assembly 104 in closed and sealed to the donut seat and, in turn, sealed to the bowl rim of the commode.

In a one embodiment of the present invention, flushing units 601 are adapted to flush commodes 603 whenever the seat assembly (top lid and antiviral filter housing) is closed and sealed. This might be achieved using an optical sensor to determine when assembly 104 (FIG. 2) is closed after use prompting a hands-free flush sequence wherein the user does not have to manually flush the commode. In this embodiment one depicted commode has the assembly 104 up. In this case, there is no command or sensed evidence to electronically flush the commode. The other depicted commode has assembly 104 shut or closed. In this case the WECM may send a wireless signal the electric flushing unit to immediately initiate a hands-free flushing sequence. In a more robust embodiment, intelligence in the form of a timing function relative to detected or communicated state events of commodes 603 may be provided to the all-electric flushing units to mitigate errors in the flushing process. For example, it is possible that a user does not manually flush the commode and does not close assembly 104. In this case a back-up routing may be observed and after a set period if the user has not closed the top lid over the donut seat, then the flushing unit 601 may override the rule of closed assembly and flush the commode with the lid open.

In one embodiment, LEDs analogous to LEDs 205 of FIG. 2 may be provided that may indicate to a user that it is safe to open the commode top lid after the last flushing sequence. Typically, that period may only be five to ten seconds long to make sure no airborne contaminants are still floating around in the commode bowl. In still a further embodiment, a servo unit might be provided that may automatically close the seat assembly 104 over the donut seat 201 (FIG. 2) by a hinge connection with a gas shock component to enable a smooth mechanical closing operation whereupon once closed and sealed the flushing unit may initiate the flush. In one embodiment, there may be a sleep mode for battery powered filter housing 104 that wakes into an operation mode based on sensor detection of movement such as a user lifting assembly 104 in preparation of using the commode 603. The sensor might be based in the filter housing 105 or in the electric flushing unit 601 without departing from the spirit and scope of the present invention.

Figure 7:
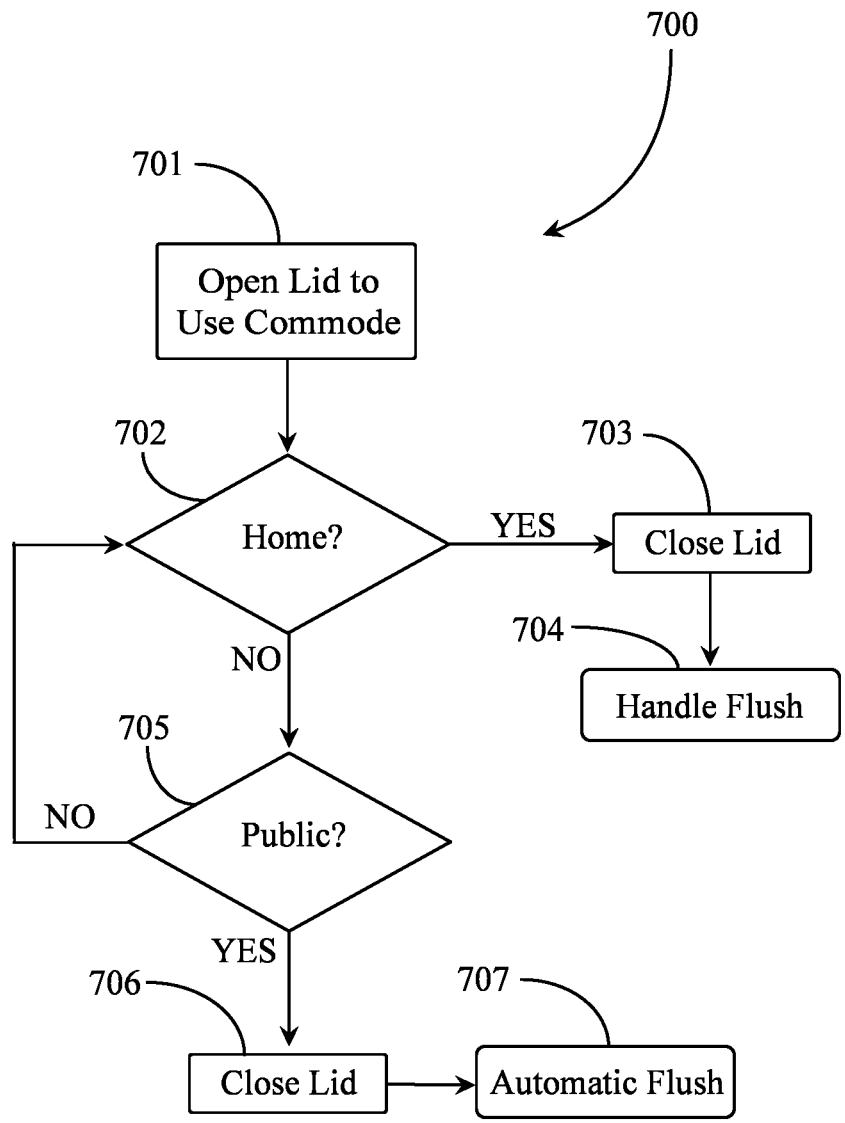
FIG. 7 is a process flow chart depicting steps for using an antiviral commode according to at least one embodiment of the present invention.

FIG. 7 is a process flow chart 700 depicting steps for using an antiviral commode according to at least one embodiment of the present invention. At step 701, a user opens the set assembly by pulling up on the assembly top lid using a handle or ledge feature breaking the seal between the filter housing and the commode donut seat. At step 702, it may be determined if the commode is a home unit or a public unit. If at step 702, the unit is a home unit, the user, once finished, closes the top lid and reseals the filter housing against the donut seat at step 703. At step 704, the user flushes the commode manually using the provided flush handle. In this simple home routine, the potentially contaminated air is filtered during the flushing process with the top lid closed.

In one embodiment, the commode has a timing function and an LED panel that uses colored light to inform the user when the top lid may be opened again.

At step 702, if it is determined the commode is not a home version, then it may be determined at step 705 if the user is operating a public version of the antiviral commode. If at step 705, the commode is a public commode, then at step 706, the user, once finished closes the lid. At step 707 an electric flushing unit initiates the flushing sequence hands free. In one aspect, when the user opens the top lid, powered electronics resident in the filter housing wake from a sleep mode and communicate with the electric flushing unit that the user is operating the commode, and the electric flushing unit may apply a timing function to authenticate actual use of the commode. In one aspect of the method using a public version of the commode, a timing function is used to flush the commode with the top lid open in an event that the user forgot to close the top lid after use and walked away. In one aspect of the public version of the commode, one or mom sensors are employed to wake the commode electronics from a sleep mode when the top lid of the commode is lifted. In this aspect, when the top lid is closed again, a counter may be employed associating the opening and closing of the top lid with a use session and may authenticate the use session with a timing function. In one aspect using the public version, the top lid is controlled mechanically by the electric flushing unit using sensors and a timing function to close the top lid in the event a user fails to close the lid after use.

It will be apparent with skill in the art that the antiviral commode system of the present invention may be provided using some or all the elements described herein. The arrangement of elements and functionality thereof relative to the smart card of the invention is described in different embodiments each of which is an implementation of the present invention. While the uses and methods are described in enabling detail herein, it is to be noted that many alterations could be made in the details of the construction and the arrangement of the elements without departing from the spirit and scope of this invention. The present invention is limited only by the breadth of the claims below.

The invention claimed is:

1. A modular antiviral air filter assembly for filtering displaced air in a flush-operated toilet, comprising:
    a ventilated filter housing;
    at least one antiviral filtering medium disposed within the filter housing
    a gasket attached to or otherwise formed on the underside of a donut rim seat of the toilet, the gasket contacting a rim surface of a collection bowl of the toilet;
    an indentation formed at a front center top surface of the donut rim seat enabling insertion of a user's fingers to lift a top lid of the assembly off of the toilet seat; and
    a control module;
    characterized in that the control module communicates with an automatic electronic flushing unit adapted to initiate flushing when a signal or sensor detects that the top lid of the assembly is in a closed position after use and
    displaced air from water filling the collection bowl after flushing is filtered through the at least one antiviral filter medium.

2. The air filter assembly of claim 1, wherein the toilet is a public or a private commode.

3. The air filter assembly of claim 1, wherein the antiviral filter is an annular air filter customized for trapping bacteria and viruses.

4. The air filter assembly of claim 1, further including two or more light emitting diodes (LEDs) for alerting a user to whether or not it may be safe to open the top cover again after a flush.

5. The air filter assembly of claim 1, wherein the donut seat has a bottom peripheral inside skirt with an angled sealing surface that mates flush with a complimentary angled sealing surface disposed about a bottom peripheral edge of the filter housing with the top lid closed, the seal method surface-to-surface or groove and O-ring gasket.

6. The air filter assembly of claim 1, wherein the ventilated filter housing includes vents in the form of one or more arrays of parallel through slots disposed proximal to a rear portion of a side wall of the top lid of the assembly.

7. The air filter assembly of claim 1, wherein the automated flushing function initiated by the automatic flushing unit is initiated with the top lid open after a period if the top lid is not closed after use.

8. The air filter assembly of claim 1, further including at least one electrostatic precipitator disposed inline at top and or beneath the filter medium.

9. The air filter assembly of claim 8, wherein the electrostatic precipitator(s) include zinc and copper rings deposited concentrically on a substrate or copper and silver dots deposited in a matrix on a substrate.

10. The air filter assembly of claim 9, wherein the substrate is a cloth material, a polymer material, or a material blend thereof.

* * * * *